(12) United States Patent
Korkor

(10) Patent No.: US 6,571,395 B1
(45) Date of Patent: Jun. 3, 2003

(54) PROTECTIVE GUARD FOR CATHETER EXIT SITE

(75) Inventor: Adel B. Korkor, Hartland, WI (US)

(73) Assignee: A. B. Korkor Medical, Inc., Hartland, WI (US)

( * ) Notice: Subject to any disclaimer, the term of this patent is extended or adjusted under 35 U.S.C. 154(b) by 0 days.

(21) Appl. No.: 10/044,396

(22) Filed: Jan. 11, 2002

(51) Int. Cl.⁷ .................................................. A61F 5/02
(52) U.S. Cl. ...................................... 2/45; 2/69; 2/104
(58) Field of Search ........................... 2/455, 459, 461, 2/463, 467, 468, 50, 82, 88, 92, 44, 45, 46, 49.1, 52, 48, 2.15, 129, 135, 141.1, 310, 913, 326, 327, 328, 104, 174; 128/846, 874, 888, 887, 849; 604/174, 179

(56) References Cited

U.S. PATENT DOCUMENTS

| 2,420,916 A | * | 5/1947 | Sorge | 2/174 |
| 2,722,685 A | | 11/1955 | Lucas | |
| 3,329,144 A | * | 7/1967 | Liman | 602/3 |
| 4,550,724 A | * | 11/1985 | Berrehail | 128/874 |
| 4,578,062 A | | 3/1986 | Schneider | |
| 4,582,508 A | | 4/1986 | Pavelka | |
| 4,891,846 A | | 1/1990 | Sager et al. | |
| 5,174,305 A | | 12/1992 | Childs | |
| 5,181,274 A | | 1/1993 | DeFiore | |
| 5,415,642 A | * | 5/1995 | Shepherd | 128/DIG. 26 |
| 5,572,740 A | | 11/1996 | Geniesse | |
| 5,592,692 A | | 1/1997 | Larson | |
| 5,605,534 A | * | 2/1997 | Hutchison | 128/849 |
| 5,720,713 A | * | 2/1998 | Hutchison | 128/849 |
| D393,737 S | | 4/1998 | Tymous | |
| D399,003 S | * | 9/1998 | Hall et al. | D24/190 |
| 5,950,235 A | * | 9/1999 | Tata | 2/48 |
| 6,226,798 B1 | * | 5/2001 | Le Blanc et al. | 2/69 |
| 6,267,115 B1 | * | 7/2001 | Marshel | 128/877 |
| 6,276,364 B1 | * | 8/2001 | Warner | 128/846 |

* cited by examiner

Primary Examiner—Gary L Welch
(74) Attorney, Agent, or Firm—Boyle Fredrickson Newholm Stein & Gratz S.C.

(57) ABSTRACT

A protective guard includes an at least substantially waterproof drape and a collar that extends upwardly from a central opening in the drape and leaves at least a substantial portion of a patient's back and chest exposed for bathing. The drape covers a catheter exit site in or near a patient's neck. In a preferred embodiment, the drape includes first and second arm portions, which cover first and second shoulder and surround at least a portion of an arm extending therefrom. The collar extends upwardly from a central opening in the drape and encircles a patient's neck. A slit in the collar permits the guard to slip past the patient's neck. Fasteners disposed on either side of the slit secure the guard to itself at an overlapping seam formed by overlapped portions of the drape. The protective guard is easily fastened and released and can be donned with one hand.

5 Claims, 6 Drawing Sheets

PROTECTIVE GUARD FOR CATHETER EXIT SITE

BACKGROUND OF THE INVENTION

1. Field of the Invention

The invention relates to protective guards, and, in particular, to protective guards for protecting catheter exit sites.

2. Description of the Related Art

Catheters are flexible tubes used for withdrawing fluids from or injecting fluids into a patient's body. For example, catheters can be used to introduce or withdraw fluids from a body cavity, duct, or vein, or artery. They are used for a variety of purposes and for differing time periods. Some catheters, such as hemodialysis catheters, are inserted into a patient's body through an incision site in or near the patient's neck or suclavion area. To prevent infection, the exit site must remain as sterile as possible. The need to protect the exit site from infection makes it difficult for a patient to bathe or otherwise go about his or her daily routine. For example, during showering, water can invade and infect the catheter exit site.

Heretofore, a hemodialysis or other central venous catheter exit sites could be protected only by covering it with a protective bandage and taping it in place. The bandage must be removed and discarded every time a catheter is used. The bandage application and removal processes are time consuming and cumbersome for the patient and/or his or her caregiver. The bandages also are often less than fully effective at preventing infection because water often seeps through them or between them and the patient's skin and enters the exit site. The protective bandage also limits the patient's mobility because it restricts the muscles surrounding the exit site.

The need therefore has arisen to provide an easy-to-use, waterproof, protective guard for a catheter incision site in or near the neck. The need has also arisen to provide a protective guard that covers the catheter exit site to protect against infection, while at the same time, allowing the patient to, for example, bathe a large portion of his or her body. The need has also arisen to provide a protective guard that extends below the catheter exit site far enough such that liquids do not splash upwardly and reach the catheter exit site.

It would also be desirable to provide an improved method of covering a catheter exit site to protect it against infection while at the same time allowing for a patient to bathe and perform other functions.

SUMMARY OF THE INVENTION

The invention, which is defined by the claims set out at the end of this disclosure, is intended to solve at least some of the problems noted above. A protective guard is provided that is designed to cover a catheter exit site in or near a patient's neck to protect against infection. At the same time, the protective guard described herein permits the patient to, for example, bathe a relatively large portion of the patient's body. The protective guard extends below the catheter exit site far enough such that liquids do not splash upwardly and reach the catheter exit site.

In a preferred embodiment, the protective guard includes a drape that covers the incision and a collar that extends upwardly from a central opening in the drape. Both the collar and the drape are preferably waterproof and sufficiently flexible so as to not unnecessarily hinder the patient's mobility. In order to remain in place during normal activity of the patient and to better protect the exit site, the drape may additionally cover one, and preferably both, shoulders of the patient as well as one and possibly both, upper arms. Straps and/or easily releasable fasteners, such as hook and loop fasteners, tape tabs, or the like, secure the various parts of the protective guard to one another to mold the guard to the patients body and hold the guard in position. Alternatively, the drape is thermally bonded to itself to form, for example, the arm covering. The fasteners preferably are located and configured so as to permit the patient to don and remove the guard preferably using just one hand.

In accordance with another aspect of the invention, a method of protecting a catheter exit site comprises 1) positioning a protective guard on the patient such that a waterproof collar of the guard snugly engages the patient's neck and a waterproof drape of the guard overlies the exit site and a portion of the patient's upper chest, shoulder, and neck located in the vicinity of the exit site, and 2) securing the protective guard in position.

Preferably, after the positioning step, an arm portion of the drape surrounds an upper portion of an arm of the patient and overlies the shoulder. In addition, a shoulder portion of the drape overlies the other shoulder of the patient while leaving an arm extending from the other shoulder uncovered.

Preferably, the positioning and securing steps are performed with one hand.

The protective guard described herein is of relatively simple construction, providing a lower cost of manufacture when compared to more complex designs. The protective guard is easy-to-use, extremely effective at protecting the exit site, flexible, and waterproof.

BRIEF DESCRIPTION OF THE DRAWINGS

Preferred exemplary embodiments of the invention are illustrated in the accompanying drawings, in which like reference numerals represent like parts throughout and in which.

Figure 1:
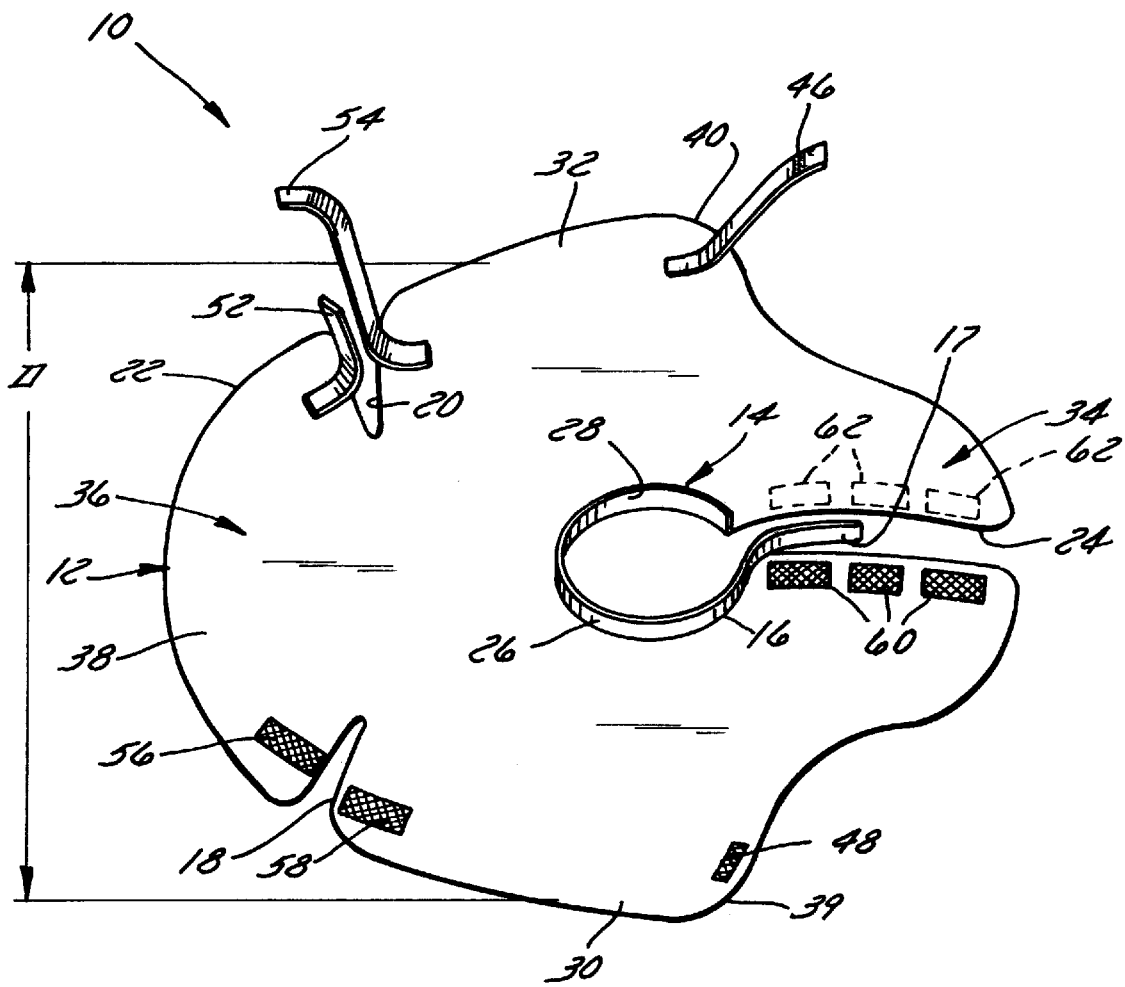
FIG. 1 is a perspective view of a protective guard constructed in accordance with a first preferred embodiment of the invention, showing the guard in an unused state thereof.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

1. Resume

Pursuant to the invention, a protective guard is provided that can be used to cover a catheter exit site in or near a patient's neck. The protective guard includes a drape and a collar that extends upwardly from a central opening in the drape. The drape may additionally cover one, and preferably both, shoulders of the patient as well as one and possibly both upper arms. Both the collar and the drape are preferably waterproof and sufficiently flexible so as to not unnecessarily hinder the patient's mobility. Straps and/or easily releasable fasteners, such as hook and loop fasteners, tape tabs, or the like secure the various parts of the protective guard to one another to mold the guard to the patient's body and to hold the guard in place. Alternatively, the drape is thermally bonded to itself to form, for example, the arm covering. The fasteners preferably are located and configured so as to permit the patient to don and remove the guard using one hand.

2. Construction and Use of a First Preferred Embodiment of Protective Guard

The protective guard described herein can be used to protect a catheter exit site in or near a patient's neck from infection. It is particularly well suited for protecting hemodialysis catheter exit sites, but can be used to protect other exit sites formed in the vicinity of a patient's neck or shoulder. At the same time, the protective guard permits access to a relatively large portion of the patient's body such that, for example, the patient can bathe a relatively large portion of the patient's body.

Figure 2:
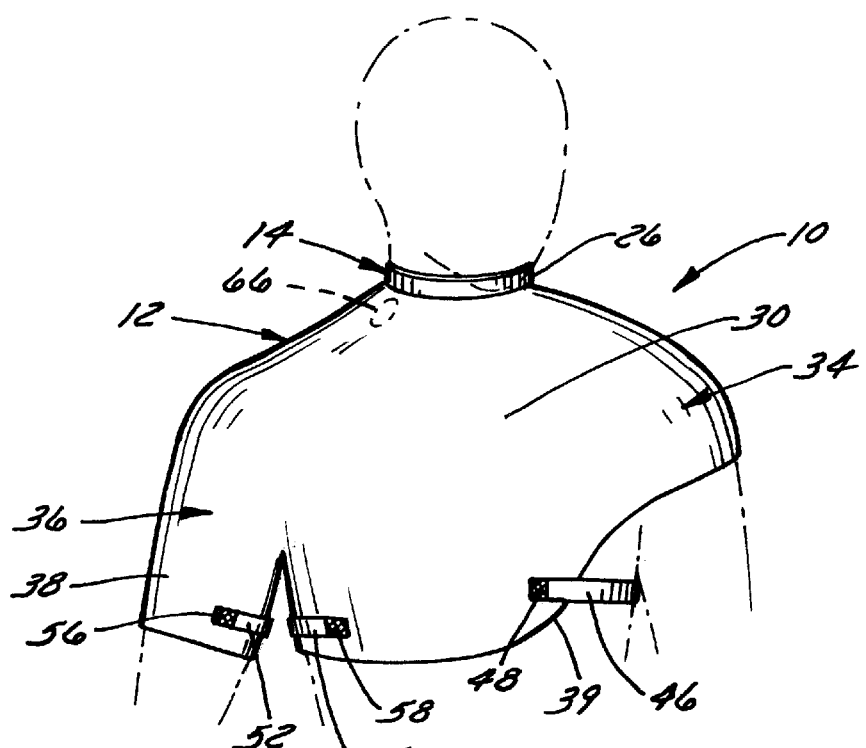
FIG. 2 is a front elevation view of a patient wearing the protective guard of FIG. 1.
Figure 3:
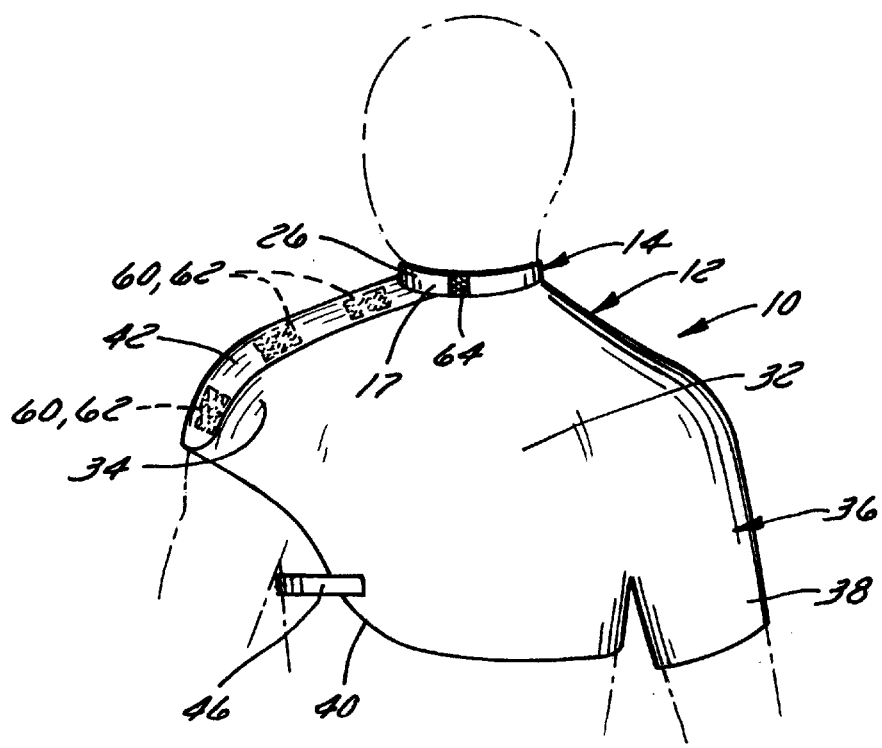
FIG. 3 is a rear elevation view of a patient wearing the protective guard of FIGS. 1 and 2.

A first preferred embodiment of the protective guard 10 is illustrated in FIGS. 1–3. The protective guard 10 includes a generally circular drape 12 and a collar 14 that extends upwardly from a central opening or cut-out 16 in the drape 12. As is shown in FIG. 1, when the protective guard 10 is laid flat, its shape is generally circular with two curved indentations 18, 20 that extend inwardly from an outer periphery 22. A radial slit 24 extends from the central cutout 16 to at or near the outer periphery 22 of the drape 12 to permit the guard 10 to be donned easily past the patient's neck. The guard 10 will typically have a mean diameter D of about 40 inches for an adult patient and about 35 inches for a child. Straps and fasteners are provided on the drape 12 and the collar 14 for releasably securing the guard 10 in place on a patient's body as detailed below.

The collar 14 is configured to fit snugly against the patient's neck so as to form a waterproof barrier without restricting the patient's breathing or reducing his or her comfort. It comprises a strip 26 formed from a relatively elastic material, preferably backed by neoprene 28 or another waterproof material such as GORE-TEX® or SYMPATEX®. Silicone can also be used as a backing. When silicone is used, it preferably has a low durometer, preferably on the order of 30 s on the D scale. Alternatively, the strip 26 itself can be formed from a waterproof material. The bottom edge of the collar 14 is molded, sewn, thermally bonded, or otherwise affixed to the periphery of the cutout 16 in the drape 12. The length of the collar 14 is longer than the circumference of the central cutout 16 such that, when the guard 10 is worn, an additional strip 17 of the collar 14 overlaps the slit 24 and part of the remainder of the collar 14 and is fastened to the remainder of the collar 14 as detailed below to hold the collar 14 in place and to seal the slit 24.

The drape 12 is formed at least in part from a flexible, sterile, waterproof material, such as 1–8 mil thick polyethylene sheet material or the like. It may be formed from a unitary sheet or an outer, decorative sheet and an inner coating formed from the flexible, waterproof material. The drape 12 includes a front portion 30 which is configured to cover the patient's ventral side, and a back portion 32 which is configured to cover the patient's dorsal side. The drape 12 also includes a shoulder portion 34 that extends outwardly from two protrusions 39 and 40 of the drape 12 and that is configured to cover the patient's left shoulder and an arm portion 36 that is configured to cover the patient's right shoulder and to form a sleeve 38 that wraps around upper portion of the patient's right arm. At the radial slit 24, the front and back portions 30, 32 of the drape 12, between the two curved protrusions 39, 40, can be overlapped such that they are coextensive for a short segment to form an overlapped seam 42 (FIG. 3) at the top of the patient's left shoulder. Complementary shoulder fasteners 60, 62 (detailed below) are disposed along the overlapped seam 42. Liquid hitting the overlapped seam 42 remains on the outside of the drape 12 to further ensure that liquid does not penetrate beneath the protective guard 10. The arm portion 36 is separated from the front and back portions 30, 32 by the indentations 18, 20. The indentations 18, 20 are generally U-shaped and are each spaced about 135° in opposite directions from the radial slit 24. They extend into the drape 12 by about 1–4" so as to permit the arm portion 36 to be wrapped around the patient's upper arm in the vicinity of his or her armpit.

The straps and fasteners are configured to securely hold the guard 10 in place when worn and to permit the guard 10 to be donned and preferably removed with one hand. All straps are affixed to the drape 12 at one end and have a hook and loop fastener; tape tabs; thin, polyurethane dressing, such as TEGADERM® brand film (3M, St. Paul, Minn.); or a similar fastener on the other end for releasable connection to a mating fastener on another location on the drape 12.

Specifically, a first strap 46 is disposed on the curved protrusion 40 at the left portion of the back portion 32 of the drape 12 and is configured to mate with a complementary fastener 48 on the other curved protrusion 39 at the front portion 30 of the drape 12 to provide a way to hold the drape 12 together at the left-hand side of the patient's chest. The strap 46 allows some flexibility in the ultimate size of the protective guard such that people of a variety of sizes can wear the protective guard 10. Second and third straps 52, 54 are mounted on opposite sides of the rear indentation 20 on the right side of the guard for mating with complementary hook and loop fasteners 56, 58 on opposite sides of the front indentation 18. Finally, mating pairs of hook and loop fasteners 60, 62 are mounted on edges of the drape 12 adjacent the slit 24 for securing the guard 10 over the patient's left shoulder at the overlapping seam 42, when the guard 10 is in use.

Referring to FIGS. 2 and 3, to don the first preferred embodiment of the guard 10, the patient widens the slit 24 in the drape 12 and collar 14 and slips it past his or her neck from the right side of the body. The patient's right arm is then inserted into the arm portion 36 of the catheter drape 12. The front and back portions 30, 32 of the drape 12 are overlapped at the left shoulder to form the overlapped seam 42 of the shoulder portion 34. The shoulder fasteners 60, 62 along the overlapped seam 42 are then secured. The extension 17 of the strip of the collar 14 is then wrapped around the patient's neck until a snug fit is achieved, and the extension 17 is then secured to a mating fastener 64 at the back of the patient's neck to form a snug, watertight fit of the collar 14 to the patient's neck. The arm portion 36 is secured about the underside of the patient's right arm by engaging the fastener on strap 52 with the fastener 56 adjacent indentation 18. The drape 12 is fastened about each side of the chest by pulling the fastener straps 46, 54 toward the front of the drape 12 until the front and back portions 30, 32 are snug. The fasteners on the fastener straps 46, 54 are then engaged with their complementary fasteners 48, 58 on the front of the guard 10. Due to the geometry of the guard 10 and the placement and configuration of the straps and fasteners, all of these tasks can be performed with one hand.

The order of securing of the various fasteners can be altered. For example, the fasteners on the right side can be engaged before those on the left side. Additionally, the handedness of the protective guard can be reversed. The above description, e.g., the shoulder portion 34 draping over the left shoulder, is for illustrative purposes only and is therefore not limiting.

The catheter exit site 66 and the area around it are now fully covered by the waterproof guard 10 as seen in FIGS. 2 and 3. The snug fit of the collar 14 around the patient's neck and the arm portion 36 around the patient's arm prevents water from seeping between the guard 10 and the patient's skin and, hence, keeps the exit site dry. Specifically, if liquid hits the side of the collar 14, such as during showering, it is deflected away from the collar 14. If liquid hits the top of the collar 14 and pools at the collar 14, it will run down the outside of the protective guard 10, preventing contact of the catheter exit site by the liquid. At the chest and the right arm, the drape 12 extends approximately 1 to 5 inches, and more preferably approximately 2 to 4 inches, below the right armpit. The protective guard 10 also extends far enough below the catheter exit site (typically 4 to 7 inches) to prevent liquids from leaching into it from below.

Because the shoulder portion 34 does not include an armhole but, instead, only extends to or near the patient's underarm, the patient's left arm is exposed to enhance the patient's mobility and to facilitate access to that arm for, e.g., bathing. A relatively large portion of the patient's upper body also is exposed as a result of the configuration, permitting showering of a relatively large area. This configuration also makes the protective guard 10 more comfortable to wear because only a relatively small percentage of the body is covered. The protective guard 10 also allows perspiration to evaporate over a large percentage of the patient's body, keeping the patient's body temperature at a more comfortable level. Conversely, by covering the right arm, the protective guard 10 is anchored such that rotation about the neck is opposed.

3. Construction and Use of a Second Preferred Embodiment of Guard

Figure 4:
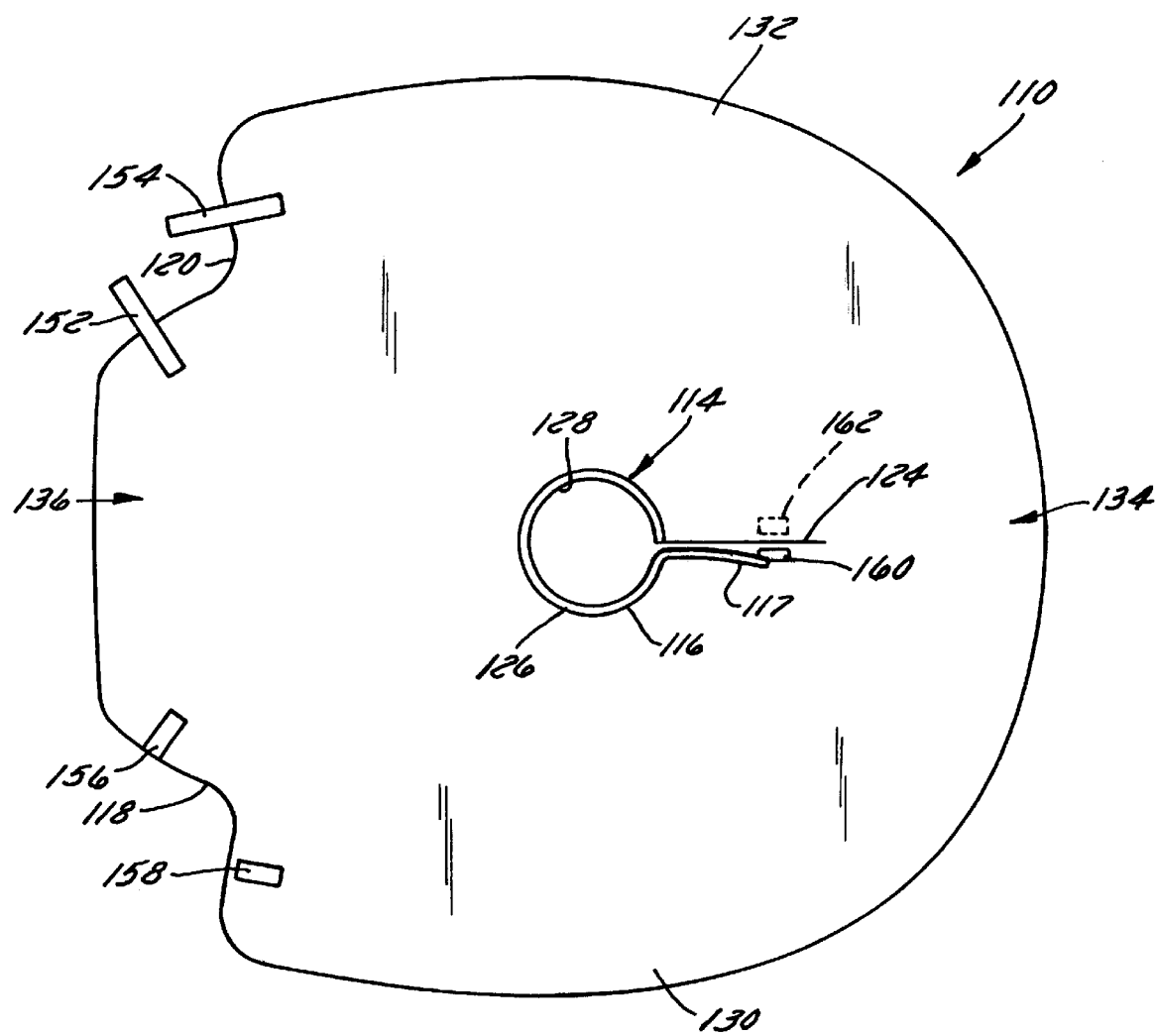
FIG. 4 is a perspective view of a protective guard constructed in accordance with a second preferred embodiment of the invention, showing the guard in an unused state thereof.

A second preferred embodiment of the protective guard 110 is illustrated in FIG. 4. Elements of the guard 110 of FIG. 4 corresponding to elements of the guard 10 of FIGS. 1–3 are, accordingly, designated by the same reference numerals, incremented by 100. The guard 110 includes curved indentations 118 and 120, a backing of neoprene 128 or another waterproof material, a slit 117, and fasteners 160 and 162. The second preferred embodiment differs from the first preferred embodiment in that it is less convoluted in shape, having a length of about 40" and a width of about 41". In addition, its slit 124 does not extend completely to the outer periphery but, instead, extends about half-way to the outer periphery. The arm portion 136 is also simpler in design, and is not flanked by cut-outs. Additionally, the straps 52 and 54 are replaced with straps 152 and 154, which mate with fasteners 156 and 158, respectively. The cut-outs of the first embodiment are also eliminated. Furthermore, the front and back portions 130, 132 of the drape 112 are not attached to each other under the shoulder portion 134, although they could be attached by fasteners or the like. The guard 110 of the second preferred embodiment is more ambidextrous than the first preferred embodiment, making it easier to use and fasten with either hand and to wrap around either arm. Hence, the guard 110 has no true "front" or "back," that is, both portions 130 and 132 each form either the front or the back.

Donning the second preferred embodiment of the guard 110 is accomplished in generally the same way as the first preferred embodiment. The differences include the following:

First, the guard 110 is slipped over the patient's head at the central opening 116 and slit 124. The collar 114 is then strapped snugly, yet comfortably, about the patient's neck using the strip 116 as in the first embodiment.

Second, the arm portion 136 is wrapped around the patient's arm and secured in place using the straps 152 and 154 and fasteners 156 and 158, with the strap 154 wrapping around the patient's side near the armpits, and strap 152 wrapping around the patient's arm near the elbow. Alternatively, the straps 152, 154 and fasteners 156 and 158 could be eliminated, and the arm portion 136 could be thermally bonded to itself at the seam formed under the patient's arm.

Third, the shoulder portion 134 on the opposite side of the guard simply overlies the opposite shoulder without having to fasten it in place. Alternatively, the shoulder portion 134 could be strapped in place using a strap and/or fasteners (not shown) as in the first embodiment.

4. Construction and Use of a Third Preferred Embodiment of Guard

Figure 5A:
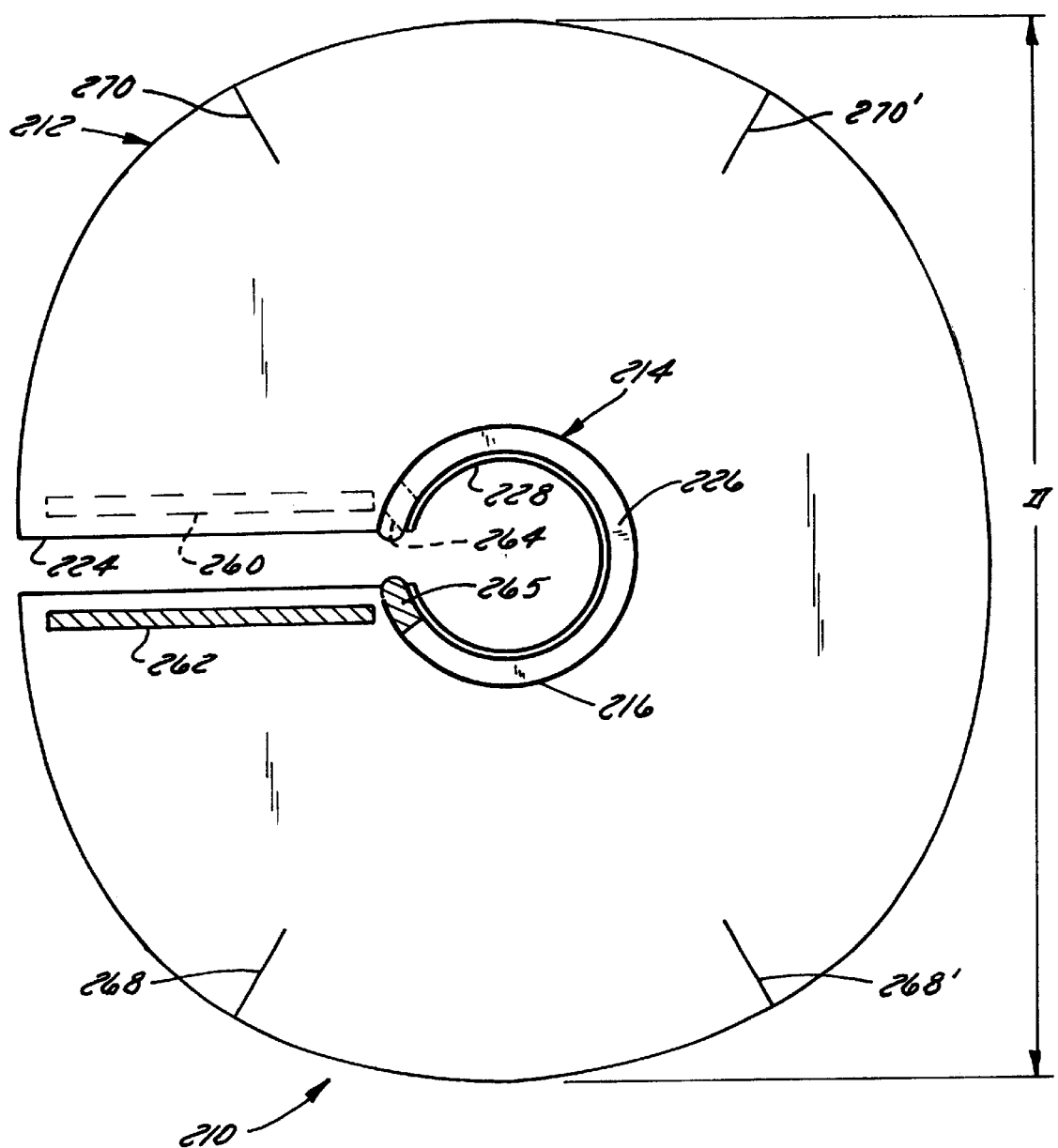
FIG. 5A is a top plan view of a protective guard in accordance with a third preferred embodiment of the invention, showing the guard prior to the formation of the arm portions.
Figure 5B:
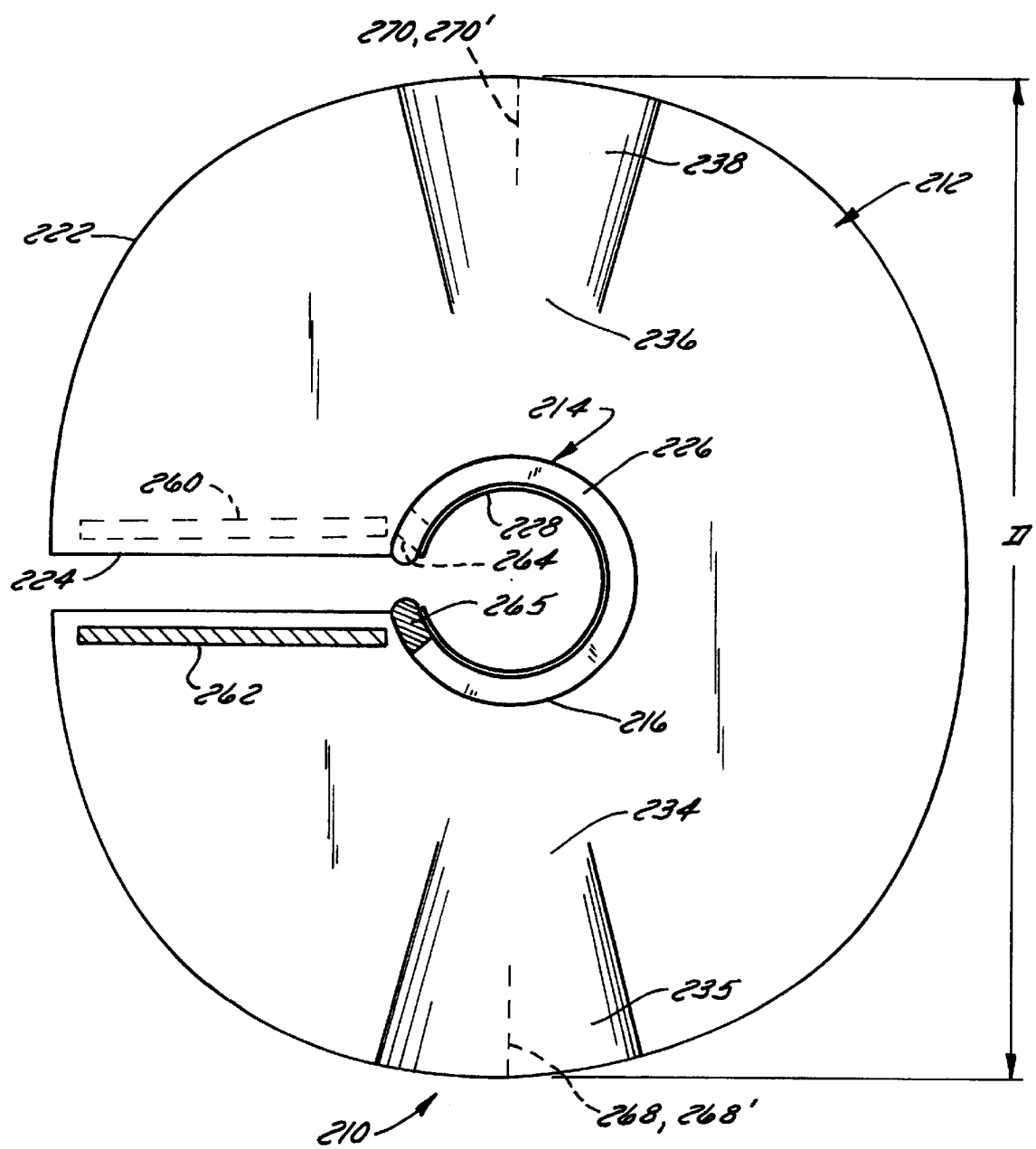
FIG. 5B is a top plan view of a protective guard of FIG. 5A, showing the guard after the formation of the arm portions.
Figure 6:
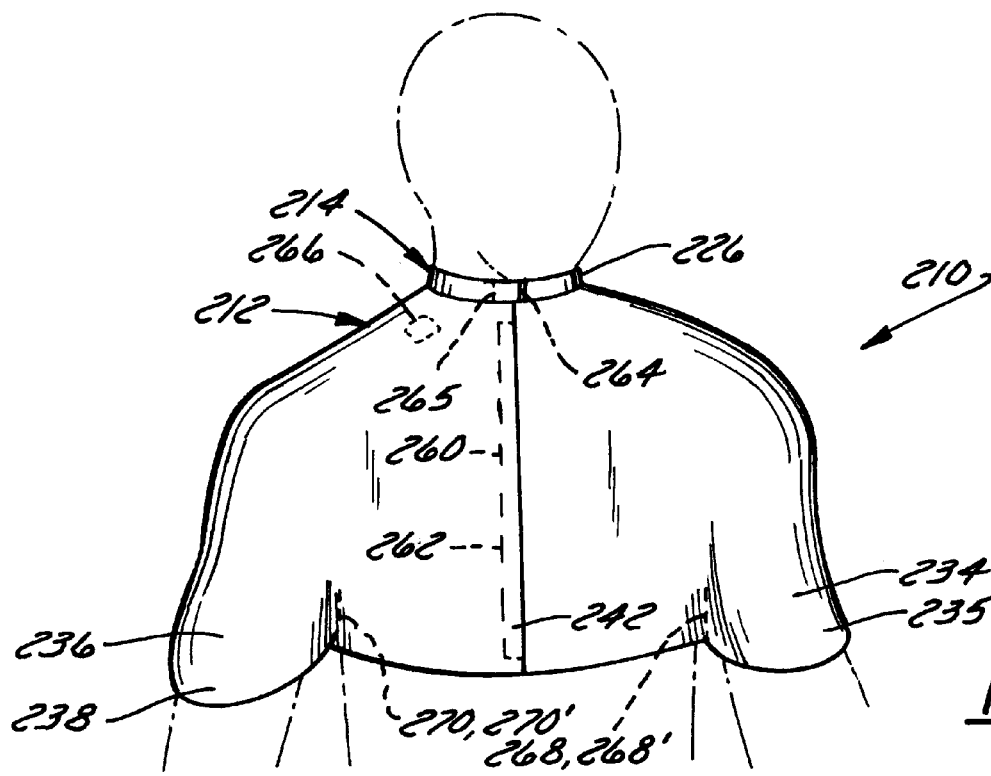
FIG. 6 is a front elevation view of a patient wearing the protective guard of FIG. 5B.
Figure 7:
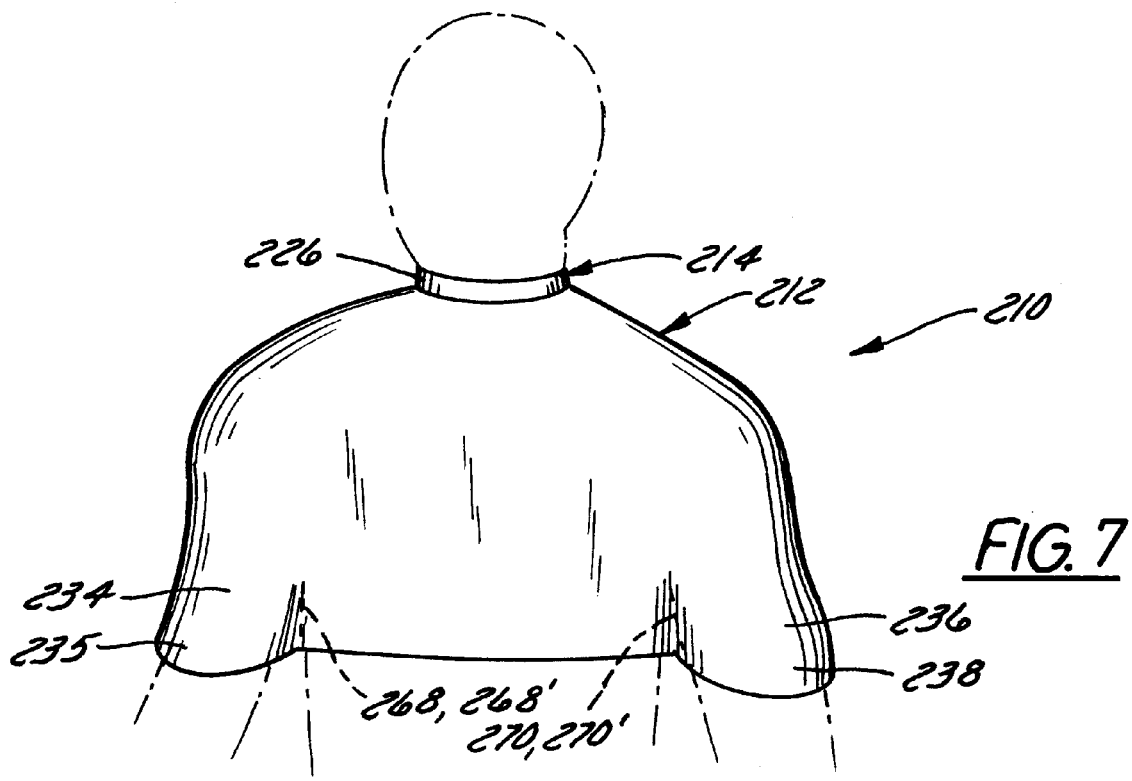
FIG. 7 is a rear elevation view of a patient wearing the protective guard of FIG. 5B.

A third preferred embodiment of the protective guard 210 is illustrated in FIGS. 5–7. The guard 210, like the guard 10 of the first embodiment, is configured to protect a catheter exit site and to keep it dry while permitting a patent to bathe and otherwise go about his or her business. Elements of the guard 210 of FIGS. 5A–7 corresponding to elements of the guard 10 of FIGS. 1–3 are designated by the same reference numerals, incremented by 200. The guard 210 covers catheter exit site 266, as is shown in FIG. 6. The guard 210 includes a generally circular drape 212 and a collar 214 that extends upwardly from a central opening or cutout 216 in the drape 212. A radial slit 224 extends from the central cutout 216 to at or near the outer periphery 222 of the drape 212 to permit the guard 210 to be donned easily past the patient's neck. The guard 210 will typically have a mean diameter D of 40 about inches for an adult patient and about 35 inches for a child. The collar 214 is configured to fit snugly against the patient's neck so as to form a waterproof barrier without restricting the patient's breathing or reducing his or her comfort. It comprises a strip 226 formed from a relatively elastic material, preferably backed by neoprene 228 or another waterproof material such as GORE-TEX® or SYMPATEX®. As in the first embodiment, silicone could also be used as a backing, or the strip 226 itself could be formed from a waterproof material. Also as in the first embodiment, the drape 212 is formed at least in part from a flexible, sterile, waterproof material, such as 1–8 mil thick polyethylene sheet material or the like. It may be formed from a unitary sheet or an outer, decorative sheet and an inner coating formed from the flexible, waterproof material.

The third preferred embodiment differs from the second preferred embodiment in that it is even less convoluted in shape, having more of a circular shape. Preferably, a pair of hook and loop fasteners 260 and 262 are mounted on edges of the drape 212 adjacent the slit 224 for securing the guard 210 at the patient's chest at the overlapping seam 242, when the guard 210 is in use. In contrast to the first and second embodiments, when the guard 210 is donned, the slit 224 is positioned at the front of the guard 210 at the center of the chest of the person wearing it. Also in contrast to the first and second embodiments, the sleeves 235 and 238 are preformed. Sleeve 235 is formed by positioning the drape 212 such that stitching lines 268 and 268' (FIG. 5A) are aligned. Lines 268 and 268' are connected, preferable by stitching, to form sleeve 235. Sleeve 238 is similarly formed by positioning the drape 212 such that lines 270 and 270' (FIG. 5A) are aligned. Lines 270 and 270' are then connected, preferable by stitching, to form sleeve 238. The constructed guard 210 is shown in FIG. 5B.

Referring to FIGS. 6 and 7, to don the third preferred embodiment of the guard 210, the patient widens the slit 224 in the drape 212 and slips it past his or her neck from the backside of the body. The patient's left arm is then inserted into the arm portion 234 and sleeve 235 of the catheter drape 212, and the patient's right arm is then inserted into the arm portion 236 and sleeve 238 of the catheter drape 212. The portions of the drape 212 on either side of the slit 224 are overlapped at the front to form the overlapped seam 242. The fasteners 260 and 262 along the overlapped seam 242 are then secured. The collar 214 is then wrapped around the patient's neck until a snug fit is achieved, and the collar 214 is then secured by mating fasteners 264 and 265 at the front of the patient's neck to form a snug, watertight fit of the collar 214 to the patient's neck. Due to the geometry of the guard 210, all of the fastening tasks can be performed with one hand.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. The invention is not intended to be limited to the preferred embodiments described above, but rather is intended to be limited only by the claims set out below. Thus, the invention encompasses all alternate embodiments that fall literally or equivalently within the scope of these claims.

What is claimed is:

1. A protective guard for covering a catheter exit site, comprising:

(a) a drape that is configured to cover a catheter exit site in or near a patient's neck and to be secured in place on the patient, the drape being at least substantially waterproof, wherein the drape includes
      an arm portion that is configured to cover a first shoulder of the patient in the vicinity of the catheter exit site and to wrap around at least an upper portion of an arm extending therefrom, and
      a shoulder portion that is configured to cover a second shoulder of the patient, wherein the shoulder portion comprises:
         (i) a front portion;
         (ii) a back portion; and
         (iii) an overlapped seam formed by overlapping the front and back portions, and further comprising fasteners that secure the front and back portions together at the overlapped seam;

(b) a collar that extends upwardly from a central opening in the drape and that is configured to encircle the patient's neck, wherein the guard is configured to leave at least a substantial portion of a patient's back and chest exposed for bathing;

(c) a strap that is configured to secure the front and back portions together at the chest under the shoulder portion;

(d) a strap that is configured to secure the front and back portions together at the chest under the arm portion; and (e) a strap that is configured to secure the front and back portions together at the arm, wherein each strap has a fastener disposed thereon that is configured for releasable attachment to a mating fastener on the drape.

2. The protective guard of claim 1, wherein the fasteners are hook and loop fasteners.

3. The protective guard of claim 1, wherein the fasteners are tape tabs.

4. A method of protecting a catheter exit site, the exit site being in the vicinity of the neck of a patient, the method comprising:

(a) slipping a slit in a protective guard past the neck of the patient, the guard including a waterproof drape and a waterproof collar that extends upwardly from a central opening in the drape, the slit extending at least part-way through the drape and through the collar, (b) surrounding the circumference of a first arm of a patient with at least a part of a first arm portion of the drape, (c) surrounding the circumference of a second arm of a patient with at least a part of a second arm portion of the drape, (d) fastening the collar about the neck of the patent in a generally watertight fashion; and (e) fastening the drape about the body of the patent in a generally watertight fashion.

5. A protective guard for covering a catheter exit site, the exit site being in the vicinity of the neck of a patient, comprising:

(a) a waterproof drape;

(b) a waterproof collar that extends upwardly from a central opening in the drape;

(c) a slit that extends at least part-way through the drape and through the collar;

(d) a first arm portion which is configured to cover a first shoulder and at least a part of which is configured to surround the circumference of an arm extending from the first shoulder; and (e) a second arm portion which is configured to cover a second shoulder and at least a part of which is configured to surround the circumference of an arm extending from the second shoulder.

\* \* \* \* \*

UNITED STATES PATENT AND TRADEMARK OFFICE
CERTIFICATE OF CORRECTION

PATENT NO. : 6,571,395 B1
DATED : June 3, 2003
INVENTOR(S) : Adel B. Korkor

It is certified that error appears in the above-identified patent and that said Letters Patent is hereby corrected as shown below:

Column 8,
Line 41, replace "patent" with -- patient --.
Line 43, replace "patent" with -- patient --.

Signed and Sealed this

Twenty-ninth Day of July, 2003

JAMES E. ROGAN
*Director of the United States Patent and Trademark Office*